US006955672B2

(12) United States Patent
Cense et al.

(10) Patent No.: US 6,955,672 B2
(45) Date of Patent: Oct. 18, 2005

(54) SKIN TREATING DEVICE WITH PROTECTION AGAINST RADIATION PULSE OVERDOSE

(75) Inventors: Abraham Josephus Cense, Cambridge, MA (US); Gerrit Jan Veldhuis, Hengelo (NL); Jan Simonsen, Struer (DK); Michiel Errit Roersma, Eindhoven (NL); Lucas Josef Maria Schlangen, Eindhoven (NL); Antonius Maarten Nuijs, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/122,740

(22) Filed: Apr. 15, 2002

(65) Prior Publication Data
US 2002/0173782 A1   Nov. 21, 2002

(30) Foreign Application Priority Data
Apr. 20, 2001  (EP) .................................. 01201432

(51) Int. Cl.$^7$ ............................................. A61B 18/18
(52) U.S. Cl. ................. 606/9; 606/10; 606/12
(58) Field of Search .................... 606/9–12

(56) References Cited

U.S. PATENT DOCUMENTS

| 4,785,806 A | * | 11/1988 | Deckelbaum | 606/7 |
| 5,628,744 A | * | 5/1997 | Coleman et al. | 606/12 |
| 6,015,404 A | * | 1/2000 | Altshuler et al. | 606/9 |
| 6,074,382 A | * | 6/2000 | Asah et al. | 606/9 |
| 6,533,774 B1 | * | 3/2003 | Ota | 606/9 |

FOREIGN PATENT DOCUMENTS

| EP | 0885629 | * | 12/1998 |
| EP | 0885629 A2 | | 12/1998 |
| EP | 1031324 | * | 8/2000 |
| EP | 1279374 | * | 1/2003 |
| WO | WO 00/62700 | * | 10/2000 |
| WO | WO0062700 | | 10/2000 |

* cited by examiner

Primary Examiner—Michael Peffley

(57) ABSTRACT

A device for the treatment of skin by radiation pulses. The device has a detector measuring a biophysical property of skin, such as temperature increase, dispersion or absorption coefficient, or reflection coefficient for light having a predetermined wavelength, and also has a control unit which determines, from the biophysical property, a safe dose of radiation. The device automatically protects against an overdose from the radiation source.

Figure 1:
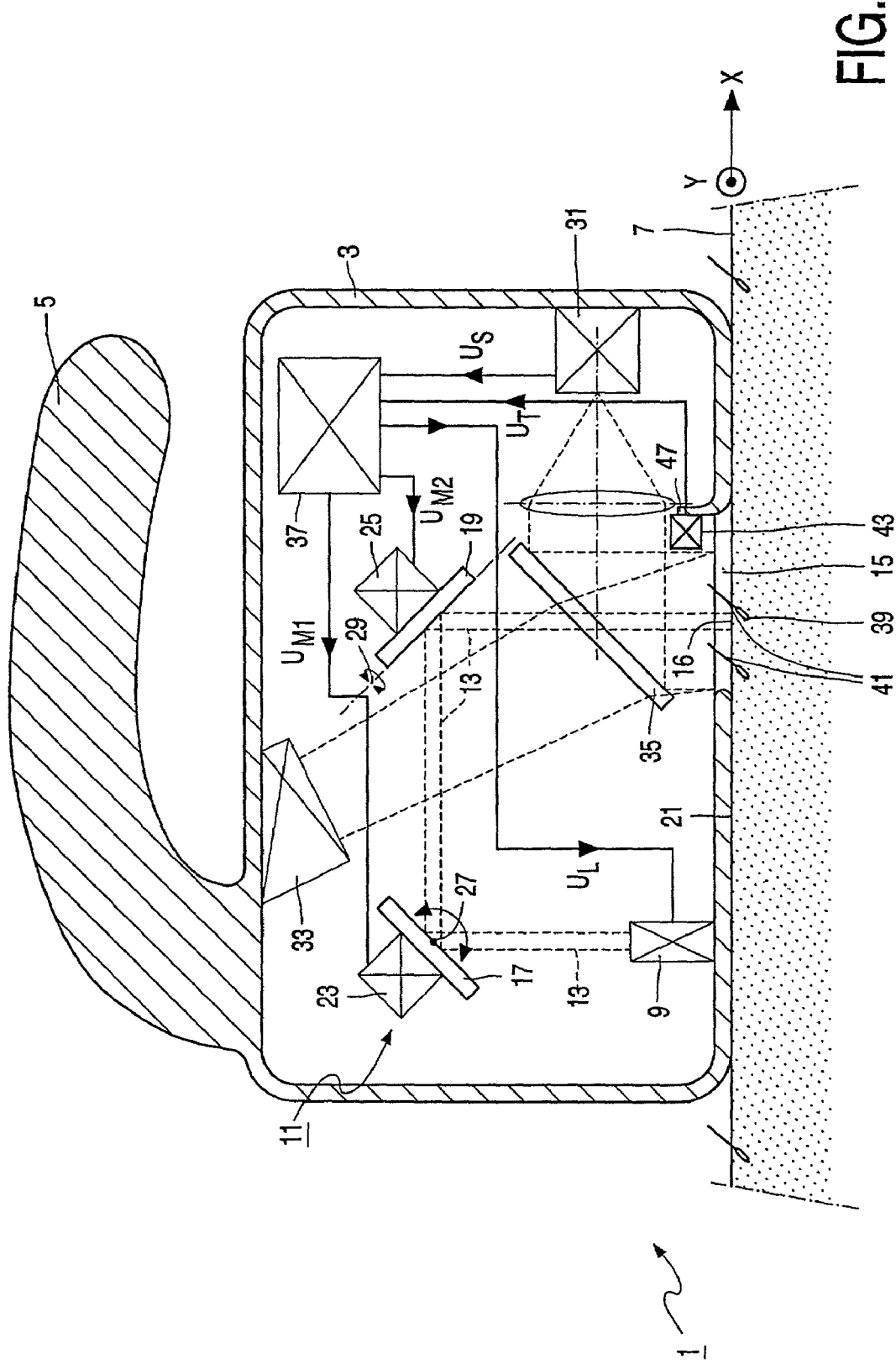

The invention can be used, not only in a hair removing device such as a laser epilator, a laser shaver or a flashlight epilator, but also in devices for the medical treatment of skin by means of radiation, such as photodermatology systems.

2 Claims, 5 Drawing Sheets

SKIN TREATING DEVICE WITH PROTECTION AGAINST RADIATION PULSE OVERDOSE

The invention relates to a device for treating skin by means of radiation pulses, which device comprises a housing, which accommodates a radiation source, and a control unit for controlling the radiation source.

A device of the type mentioned in the opening paragraph is known from WO-A-00/62700. Said known device is a hair removing device, in particular a laser epilation device, by means of which hairs present on the skin are removed for a comparatively long period of time or permanently by means of laser pulses. The radiation source of the known device is a laser source. The housing of the device is provided with an exit opening, which is to be placed on the skin to be treated. The laser source generates a laser beam, which, by means of a laser beam manipulator, is positioned in a target position on the skin via the exit opening. The target position corresponds to a position of a hair root in the skin and is established by the control unit from an image of the skin that is recorded by means of an image sensor that is also arranged in the housing. The control unit successively sends the laser beam manipulator to all target positions established from the image, the laser source being activated, in each target position, by the control unit so as to generate a laser pulse of a predetermined pulse dose, i.e. a predetermined duration and intensity. As a result, the hair roots present in front of the exit opening are successively heated, causing said hair roots to die. As the target positions are automatically determined, the device can particularly suitably be used for the consumer market, i.e. the device is suitable for non-professional use.

In the known device, the laser pulses generated by the laser source have a predetermined pulse dose that is so high that the hair types that are most common in practice die under the influence of the laser pulses. A drawback of the known device is that the laser pulses may have undesirable side-effects on the skin present around the hair roots, such as skin irritations and pain. In the case of sensitive skin types, even small burns or pigment changes may be caused.

It is an object of the invention to provide a device of the type mentioned in the opening paragraph, which is protected against an overdose of the radiation pulses that would be impermissible because of its effect on the skin, so that the above-mentioned drawback of the known device is precluded as much as possible.

To achieve this object, a device of the type mentioned in the opening paragraph is characterized in accordance with the invention in that the device comprises a detector for measuring a biophysical property of the skin, the control unit comprising means which enable a pulse dose from the radiation source that is permissible for the skin to be determined on the basis of a value or condition of the property measured by means of the detector. The effects that radiation pulses having a predetermined pulse dose have on the skin, and particularly the maximum permissible radiation pulse dose at which undesirable side-effects on the skin do not occur, depend on the biological composition of the skin and differ from skin type to skin type. These effects predominantly depend on the quantity and distribution of melanin in the skin. These effects additionally depend on the quantity and distribution of blood, water and keratin in the skin. The value or condition of a large number of biophysical properties of the skin is at least partly determined by the quantity and distribution of said substances in the skin. By measuring, by means of said detector, the value or condition of a suitable biophysical property of the skin, i.e. a property that depends comparatively strongly on the quantity and distribution of said substances in the skin, it is possible to determine, by means of the control unit, a pulse dose from the radiation source that is safe for the skin type to be treated, for example on the basis of an empirically predetermined relation between said biophysical property and the permissible pulse dose. In this manner, a reliable protection against an overdose of the radiation pulses that is impermissible for the skin is achieved. As the maximum permissible pulse dose is automatically adapted to the skin type, the suitability of the device for the consumer market is increased.

A particular embodiment of a device in accordance with the invention is characterized in that the control unit determines, in operation, the permissible pulse dose before it activates the radiation source for treating the skin. As the control unit determines the permissible pulse dose before the radiation source is activated for treating the skin, protection against an impermissible overdose of the radiation pulses is provided throughout the skin treating process.

A further embodiment of a device in accordance with the invention is characterized in that the means comprise a comparator for comparing the measured value or condition of the biophysical property with a relation between the property and the permissible pulse dose, which relation is stored in a memory of the control unit. The relation stored in the memory is, for example, previously established in an accurate, empirical way. In this manner, an accurate and reliable protection against an impermissible overdose of the radiation pulses is provided.

A still further embodiment of a device in accordance with the invention is characterized in that the detector can suitably be used to measure a temperature of the skin resulting from exposure to a test radiation pulse having a predetermined pulse dose. In this embodiment, preferably before treating the skin, at least one test radiation pulse is generated having a predetermined, relatively low and safe pulse dose. The measured value of the temperature of the skin caused by exposure to this test radiation pulse is compared by the control unit with, for example, reference values that have been previously established for a large number of different skin types. As said reference values depend strongly on the skin type, the skin type and hence the permissible pulse dose of the radiation source are very accurately and reliably determined by using said detector, so that a very accurate and reliable protection against an impermissible overdose of the radiation pulses is provided.

A particular embodiment of a device in accordance with the invention is characterized in that the detector can suitably be used to measure a variation of the temperature as a function of time. The measured variation in temperature as a function of time, in particular the maximum temperature value that can be derived therefrom and the moment at which this maximum value is attained, enable the skin type and the permissible pulse dose of the radiation source to be derived in an even more reliable manner.

A further embodiment of a device in accordance with the invention is characterized in that, in operation, the radiation source generates the test radiation pulse. By virtue thereof, the number of parts of the device is limited, so that the structure of the device is simple.

Yet another embodiment of a device in accordance with the invention is characterized in that the radiation source generates a series of test radiation pulses having increasing, predetermined pulse doses, the detector measuring the temperature after each test radiation pulse generated, and the control unit terminating the series if the temperature reaches a predetermined critical value. It has been found that undesirable side-effects of the radiation pulses on the skin occur predominantly if the temperature of the skin caused by exposure to radiation pulses rises above a critical value. It has also been found that this critical value is substantially equal for the most common skin types. In this embodiment, the control unit increases the pulse dose of the test radiation pulses until the measured skin temperature has reached said critical value. In this manner, the permissible pulse dose is established in a reliable and accurate way. In this embodiment, the structure of the control unit is comparatively simple because the skin properties stored in the memory predominantly comprise only said critical temperature value.

A particular embodiment of a device in accordance with the invention is characterized in that the detector comprises an infrared sensor. By means of the infrared sensor the temperature of the skin can be accurately measured and without mechanical contact with the skin. The infrared sensor is comparatively inexpensive and has small dimensions, as a result of which the cost-price and the dimensions of the detector are limited.

A further embodiment of a device in accordance with the invention is characterized in that the detector can suitably be used to measure a scattering coefficient and/or absorption coefficient of the skin for the radiation. It has been found that there is a relation that can be clearly established between, on the one hand, the scattering coefficient and/or absorption coefficient of the skin for radiation of a predetermined wavelength and, on the other hand, the amount and distribution of melanin, keratin, blood and water in the skin. As a result, it is also possible to establish a clear relation between, on the one hand, said scattering coefficient and/or absorption coefficient and, on the other hand, the pulse dose from the radiation source that is permissible for the skin. Thus, using said detector, the pulse dose that is permissible for the skin can be established in a reliable manner.

A still further embodiment of a device in accordance with the invention is characterized in that the detector can suitably be used to measure a reflection coefficient of the skin for the radiation. It has been found that also a relation between on the one hand the reflection coefficient of the skin for radiation having a predetermined wavelength and, on the other hand, the quantity and distribution of melanin, keratin, blood and water in the skin can be clearly established. As a result, it is also possible to establish a clear relation between said reflection coefficient and the pulse dose from the radiation source that is permissible for the skin. Thus, by means of said detector, it is also possible to reliably determine the pulse dose that is permissible for the skin.

A particular embodiment of a device in accordance with the invention is characterized in that the detector is provided with a light sensor and a light source for light of a predetermined wavelength, which light source is optically separated from the light sensor. As the light source is optically separated from the light sensor, the light from the light source cannot directly reach the light sensor. In an embodiment wherein the light source and the light sensor are situated, in operation, so as to be in contact with the surface of the skin, however, the light from the light source can reach the light sensor by scattering in the skin. In an embodiment where the light source and the light sensor are situated, in operation, at a distance from the surface of the skin, the light from the light source can reach the light sensor by reflection via the surface of the skin. In this manner, using the detector, the scattering coefficient and/or absorption coefficient of the skin for said light, and the reflection coefficient of the skin for said light, respectively, can be measured in a reliable manner.

A further embodiment of a device in accordance with the invention is characterized in that the light source is an LED and the light sensor is a photodiode. Said LED and photodiode are comparatively inexpensive and have small dimensions, as a result of which the cost-price and dimensions of the detector are limited.

A still further embodiment of a device in accordance with the invention is characterized in that the device is a hair removing device, wherein the radiation source comprises a laser source, and wherein the device is further provided with an adjustable laser beam manipulator for positioning a laser beam supplied, in operation, by the laser source in a target position on the skin to be treated. In this embodiment of the device in accordance with the invention, the invention becomes effective in a particular way since the laser beam generated by the laser source has a comparatively high intensity and hence, in the event of an overdose, could readily lead to undesirable side-effects on the skin if no additional measures are taken.

A particular embodiment of a device in accordance with the invention is characterized in that the device is a hair removing device, wherein the radiation source comprises a flashlight for generating light pulses, and wherein the device is further provided with a directing element for directing the light pulses to an exit opening provided in the housing. In this embodiment of the device in accordance with the invention, the invention also becomes effective in a particular way as the light pulses generated by the flashlight have a comparatively high intensity and hence, in the event of an overdose, could readily lead to undesirable side-effects on the skin if no additional measures are taken.

Figure 2:
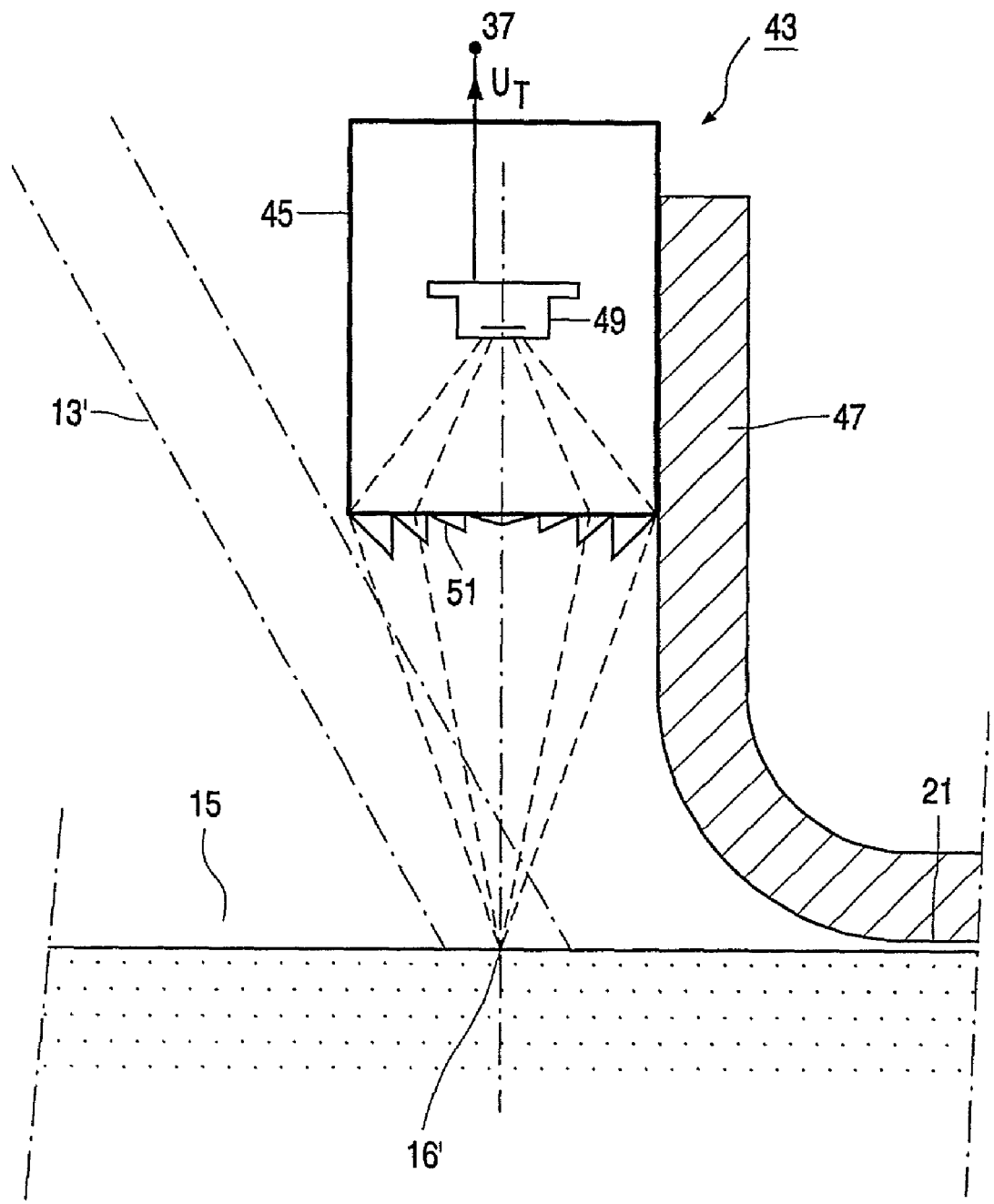
Figure 3:
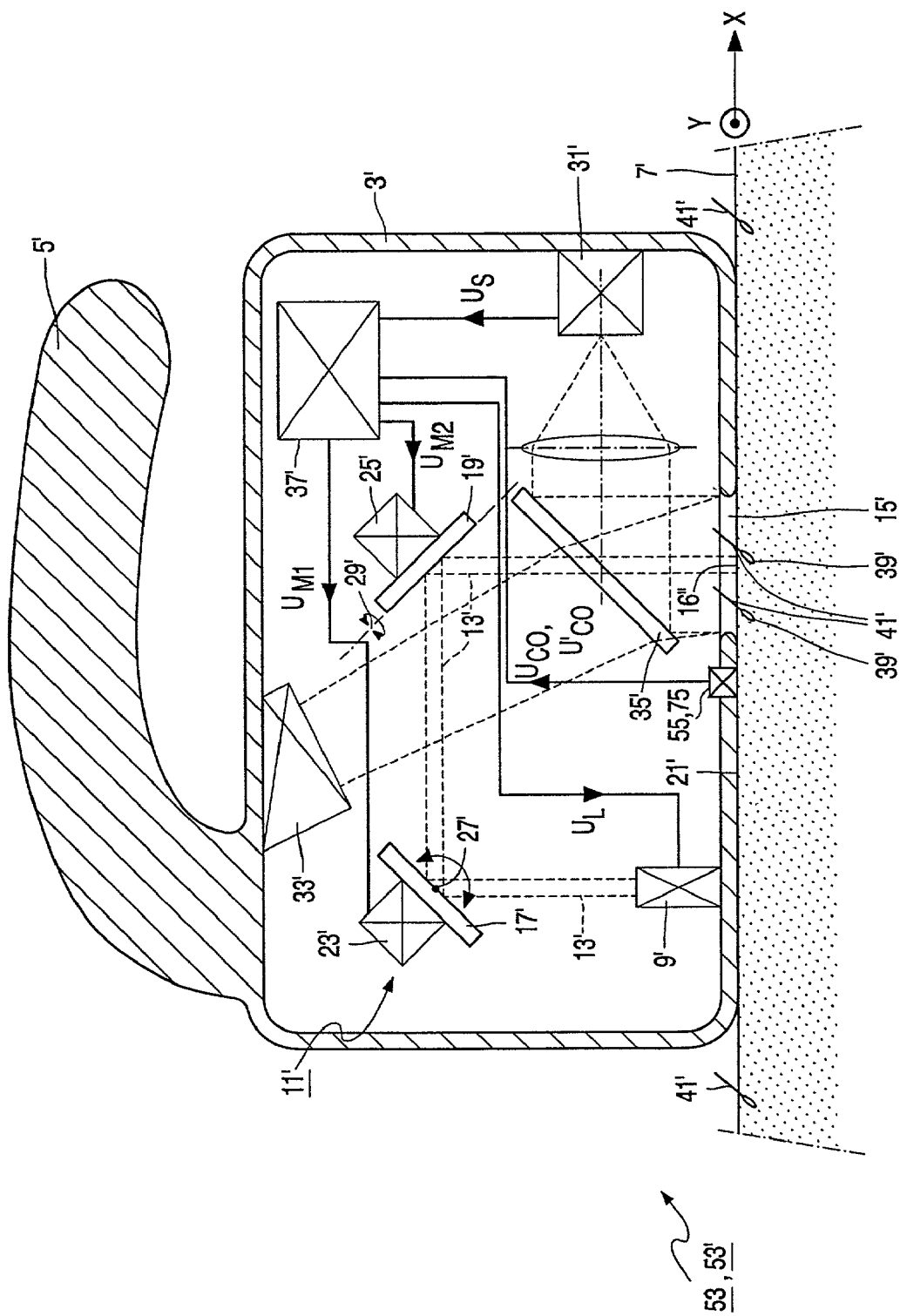
Figure 4:
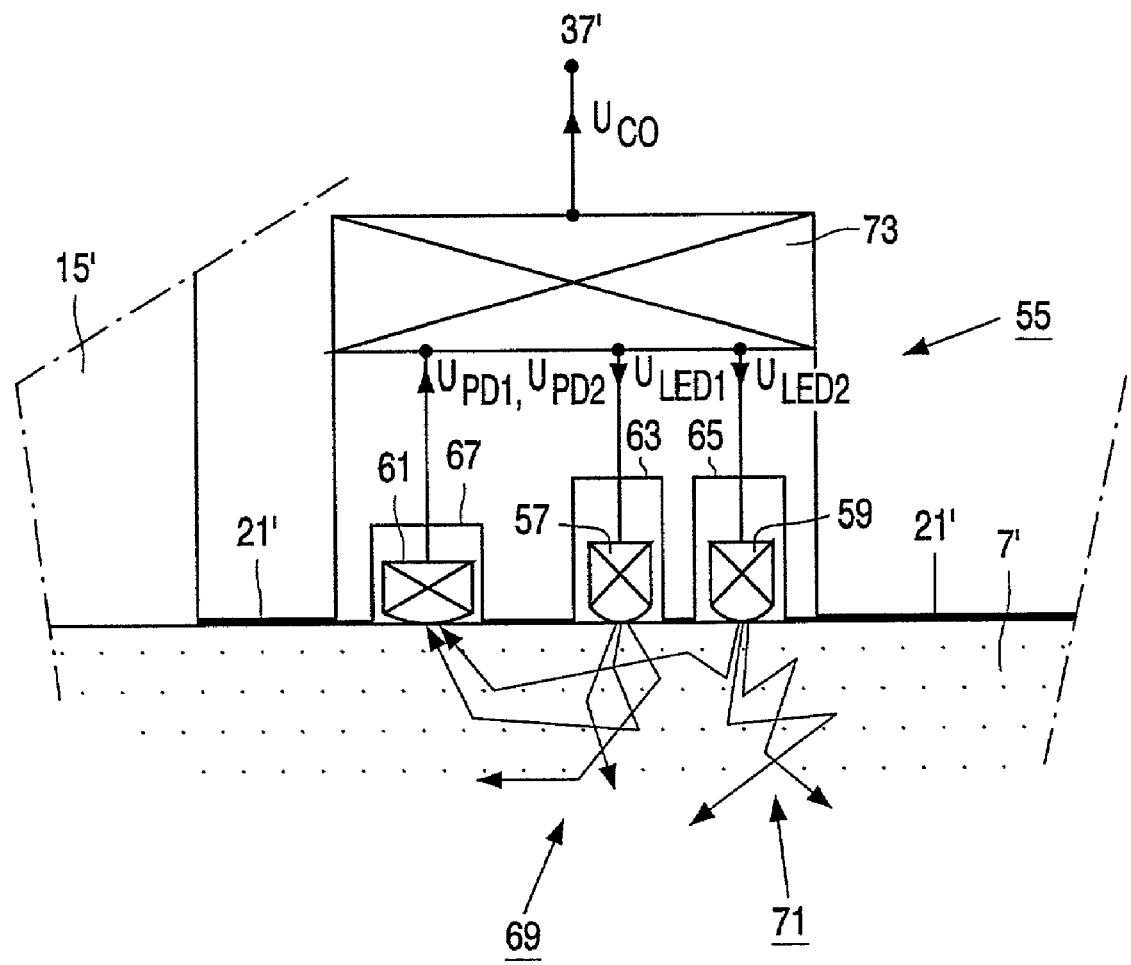
Figure 5:
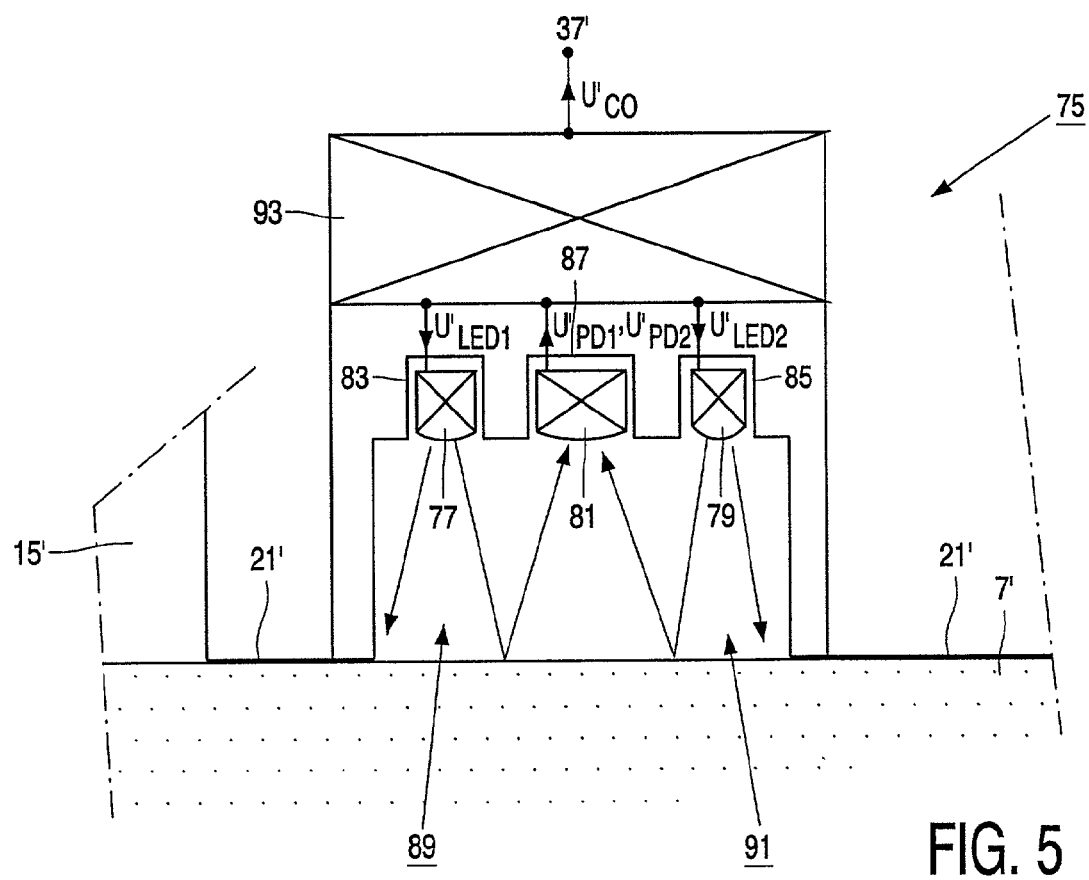
Figure 6:
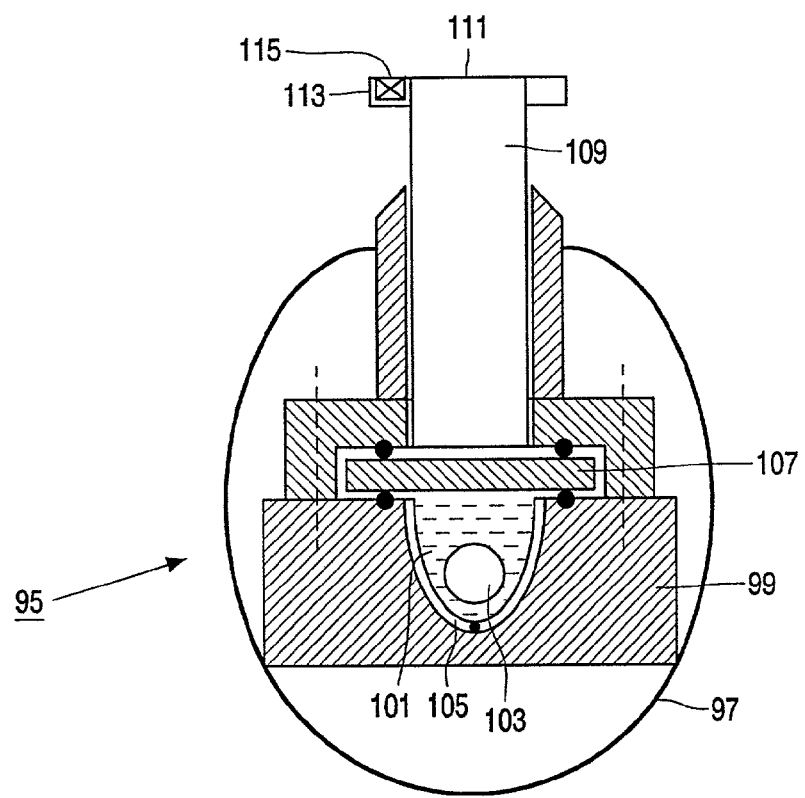

In the following, embodiments of a device for treating skin by means of radiation pulses according to the invention will be explained in detail as shown in the figures, wherein:

FIG. 1 diagrammatically shows a first example of a device in accordance with the invention, FIG. 2 diagrammatically shows a detector of the device in accordance with FIG. 1, FIG. 3 diagrammatically shows a second example of a device in accordance with the invention, FIG. 4 diagrammatically shows a detector of the device in accordance with FIG. 3, FIG. 5 diagrammatically shows a detector of a third example of a device in accordance with the invention, and FIG. 6 diagrammatically shows a fourth example of a device in accordance with the invention.

FIG. 1 diagrammatically shows a first example of a device 1 in accordance with the invention for treating skin by means of radiation pulses, said device being a hair removing device, in particular a laser epilation device, by means of which hairs present on the skin are removed for a comparatively long period of time or permanently by means of laser pulses. Said device 1 comprises a housing 3 with a handle 5, so that the device 1 is portable and can be placed on or moved over skin 7 to be treated. The housing 3 accommodates a radiation source, in particular a laser source 9 such as a diode laser, and an adjustable laser beam manipulator 11 by means of which a laser beam 13 generated, in operation, by the laser source 9 can be positioned, via an exit opening 15 provided in the housing 3, on the skin 7 in a target position 16. In the example shown, the laser beam manipulator 11 comprises a first adjustable tilting mirror 17 and a second adjustable tilting mirror 19, which are both arranged at an angle of approximately 45° with respect to a flat skin contact element 21, in which the exit opening 15 is situated and which, in the example shown, forms a bottom wall of the housing 3. By means of a first actuator 23 and a second actuator 25, the tilting mirrors 17 and 19, respectively, can be tilted about, respectively, a first tilt axis 27, which extends in the plane of the first tilting mirror 17 and is directed substantially parallel to the second skin contact element 21, and a second tilt axis 29, which extends in the plane of the second tilting mirror 19 and intersects the first tilt axis 27 substantially perpendicularly. By tilting the two tilting mirrors 17 and 19, the target position 16 of the laser beam 13 can be displaced over the skin 7 in a direction parallel to an X-direction and a Y-direction extending perpendicularly thereto, both directions being parallel to the skin contact element 21.

To determine successive target positions, the device 1 is provided, in the example shown, with an image sensor 31, such as a CCD image sensor or CMOS image sensor, which records an image of the part of the skin 7 that is situated directly in front of the exit opening 15, by means of an auxiliary lamp 33 and a transparent mirror 35. The device 1 further comprises a control unit 37 to which the image sensor 31 supplies an electrical signal $u_S$ which corresponds to the image recorded by the image sensor 31. The control unit 37 comprises a processor by means of which, on the basis of the image recorded, the positions of the hair roots 39 of the hairs 41 present on said part of the skin 7 are determined on said part of the skin 7. The control unit 37 controls the two actuators 23 and 25 by means of, respectively, an electrical signal $u_{M1}$ and an electrical signal $u_{M2}$, in such a manner that the laser beam 13 is successively positioned in a series of target positions that correspond to the positions of the hair roots 39 thus determined. In each target position 16, the laser source 9 is activated by the control unit 37 by means of an electrical signal $U_L$ so as to generate a laser pulse having a predetermined pulse dose, i.e. during a predetermined period of time and with a predetermined intensity. The intensity of the pulse dose is so high that the hair roots 39 present are successively heated in such a manner that they die. As the target positions are automatically determined, the device 1 can particularly suitably be used for the consumer market, i.e. for non-professional users. For a detailed explanation of the operation of the device 1, which is only briefly described herein, reference is made to WO-A-00/62700.

The above-mentioned pulse dose is previously established in an empirical way and is so high that the hair types that are most common in practice die under the influence of the laser pulses. In accordance with the invention, the device 1 comprises, however, a protection against an impermissible overdose of the laser pulses that could have undesirable side-effects on the skin present around the hair roots 39, such as skin irritations, pain and, in the case of sensitive skin types, even small burns or pigment changes. The effects of laser pulses having a predetermined pulse dose on the skin, and in particular the pulse dose of the laser pulses that is permissible for the skin and does not lead to undesirable side-effects, depend on the biological composition of the skin and differ from skin type to skin type. These effects depend predominantly on the quantity and distribution of melanin in the skin and, furthermore, on the quantity and distribution of blood, water and keratin in the skin. In general, the permissible pulse dose decreases as the amount of these substances in the skin increases, particularly as the amount of melanin increases. This can be attributed to the fact that laser light is absorbed comparatively strongly by, in particular, melanin, so that the temperature of the skin increases comparatively strongly. It has been found that undesirable side-effects of the laser pulses on the skin occur predominantly if the temperature of the skin rises above a critical value. It has further been found that this critical value is substantially equal for the skin types that are most common, namely approximately 52° C.

In the device 1, protection against an impermissible overdose of the laser pulses is achieved by using a detector 43 which can suitably be employed to measure a temperature of the skin resulting from exposure to a series of test laser pulses. As is shown in FIG. 2, the detector 43 comprises, in the example shown, a detector housing 45 which is attached, at some distance from the skin contact element 21, to an upright edge 47 of the exit opening 15. The detector housing 45 accommodates an infrared sensor 49. A Fresnel lens 51 is situated between the infrared sensor 49 and the exit opening 15. The control unit 37 establishes, in operation, the permissible pulse dose before said control unit 37 activates the laser source 9 so as to remove the hairs 41 present. For this purpose, the control unit 37 controls the laser beam manipulator 11 in such a manner that the target position 16' of the laser beam 13' is initially situated directly in front of the detector 43, as shown in FIG. 2. Subsequently, the control unit 37 controls the laser source 9 in such a way that the laser source 9 generates a series of test laser pulses having increasing, predetermined pulse doses. After each generated test laser pulse, the detector 43 measures the temperature of the skin in the target position 16', which target position is approximately in the focus of the Fresnel lens 51. The Fresnel lens 51 is comparatively thin and made of a material having a comparatively low absorptivity for infrared radiation, polyethylene in the example shown, so that as much heat as possible of the skin present in the target position 16' is focused on the infrared sensor 49. The detector 43 generates an electrical signal $u_T$, which corresponds to the temperature measured and is supplied to the control unit 37. The control unit 37 subsequently ends the series of test laser pulses if the temperature measured reaches said critical value of 52° C. or a safe limiting value of, for example, 51° C. The control unit 37 determines that the pulse dose at which said critical value or limiting value of the temperature is reached is the permissible pulse dose. As said critical value of the temperature is a reliable limiting value as regards the development of undesirable side-effects of the laser pulses on the skin, the permissible pulse dose is accurately and reliably determined in the manner described hereinabove. Said critical value or limiting value of the skin temperature is the only property of the skin that is to be stored in a memory of the control unit 37, so that the structure of the control unit 37 is comparatively simple. By means of the infrared sensor 49, the temperature of the skin is accurately determined. Said infrared sensor 49 is comparatively inexpensive and has limited dimensions, as a result of which the cost-price and the dimensions of the detector 43 are limited. In the example shown, the detector 43 measures a variation of the temperature of the skin as a function of time. The value of the temperature, which is compared with the critical value by the control unit 37, is a maximum value of the temperature that is determined by the control unit 37 from the measured variation of the temperature. In this manner, the reliability and accuracy with which the permissible pulse dose is determined is further increased. It is noted that the invention also comprises embodiments wherein determining the maximum value of the temperature from the measured temperature variation is carried out by a processor that forms part of the detector 43. The invention further includes embodiments wherein the test laser pulses are generated by an independent light source whose frequency corresponds to the frequency of the laser source 9. As, in the device 1, the test laser pulses are generated by the laser source 9, the number of components of the device 1 is limited, resulting in a simple structure of said device 1. As the control unit 37 thus determines the permissible pulse dose before activating the laser source 9 to remove the hairs 41, protection against an impermissible overdose of the laser pulses is provided during the entire hair removing process.

It is noted that the invention also comprises embodiments wherein the detector 43 is employed in a different way to establish the permissible pulse dose from the laser source 9. An example of such a different way of employing the detector 43 is an embodiment wherein, prior to the hair removing process, the laser source 9 generates one or a comparatively small number of test laser pulses having a predetermined, comparatively low, safe pulse dose, and wherein the temperature measured by means of the detector 43, which is the temperature of the skin resulting from exposure to these test laser pulses, is compared by the control unit 37 with reference temperatures which are previously, empirically established for a large number of skin types by exposing these skin types to a comparable test laser pulse. In such an embodiment, the control unit 37 comprises a memory wherein said reference temperatures are stored, and a comparator that compares the skin temperature measured by the detector 43 with said reference temperatures. The control unit 37 subsequently determines that the permissible pulse dose is the permissible pulse dose associated with a skin type whose reference temperature corresponds to the measured temperature. Another example of a different way of employing the detector is an embodiment wherein the variation in temperature of the skin caused by exposure to a predetermined test laser pulse and measured by the detector 43 is used by the control unit 37 to determine, apart from the maximum temperature, the moment at which the maximum temperature is achieved, and in which embodiment the control unit 37 compares the measured maximum temperature and the measured moment with reference temperatures and reference moments which are previously empirically established for a large number of skin types. As the above-mentioned reference temperatures and reference moments can be accurately determined and, in addition, depend substantially on the skin type, the permissible pulse dose can be accurately and reliably determined in the above-mentioned alternative embodiments.

In the above-described embodiments of a device in accordance with the invention, the permissible pulse dose of the laser pulses is determined on the basis of a measured temperature of the skin caused by exposure to a predetermined test laser pulse. The invention also comprises embodiments wherein the permissible pulse dose is determined by measuring another biophysical property of the skin. In the second example of a device 53 in accordance with the invention, as shown in FIG. 3, the permissible pulse dose is determined by measuring a scattering coefficient and/or absorption coefficient of the skin for light of a predetermined wavelength. The device 53, like the device 1 discussed hereinabove, is a laser epilation device and, in FIG. 3, parts of the device 53 corresponding to parts of the device 1 are indicated by means of corresponding reference numerals. The device 53 differs mainly from the device 1 in that the device 53 is provided with a detector 55, instead of the above-discussed detector 43, which detector 55 can suitably be used to measure the scattering coefficient and/or absorption coefficient of the skin for light of a predetermined wavelength. Said wavelength is, for example, equal to the wavelength of the laser source 9' but may also be different, as is the case in the example shown. The detector 55 is provided in the skin contact element 21' near the exit opening 15'. As is shown in FIG. 4, the detector 55 comprises, in the example shown, two light sources 57, 59, which are LEDs in the example shown, emitting light of two different, predetermined wavelengths, and a single light sensor 61, which is a photodiode in the example shown, which is arranged next to the light sources 57, 59. The light sources 57, 59 and the light sensor 61 are each provided in a separate chamber 63, 65, 67 of the detector 55, as a result of which the light sensor 61 is optically separated from the light sources 57, 59, i.e. light from the light sources 57, 59 cannot directly reach the light sensor 61. On the other hand, as is shown in FIG. 4, light beams 69, 71 from the light sources 57, 59 can reach the light sensor 61 through scattering in the skin if, in operation, the device 53 is in contact, via the skin contact element 21', with the skin 7' to be treated. The detector 55 further comprises an electrical circuit 73 which successively activates the two light sources 57, 59 for a short period of time by means of two electrical signals $u_{LED1}$ and $u_{LED2}$. As a result, the circuit 73 successively receives two electrical signals $u_{PD1}$ and $u_{PD2}$ from the light sensor 61, which electrical signals correspond to the amounts of light received by the light sensor 61, through scattering in the skin 7', from the two light sources 57 and 59, respectively. The circuit 73 subsequently determines the values of the scattering coefficient and/or absorption coefficient of the skin 7' for said two different wavelengths of the two light sources 57, 59 by comparing the amounts of light received with the amounts of light generated by the light sources 57, 59 and determined by the signals $u_{LED1}$ and $u_{LED2}$. The circuit 73 converts the values of the scattering coefficient and/or absorption coefficient thus measured into an electrical signal $u_{CO}$ which, as shown in FIG. 3, is received by the control unit 37' of the device 53. The control unit 37 comprises a comparator, not shown in the Figures, which compares the measured values of the scattering coefficient and/or absorption coefficient with reference values which have been previously, empirically established for a large number of skin types and which are stored in a memory of the control unit 37'. The control unit 37' subsequently determines that the permissible pulse dose from the laser source 9', is the pulse dose which is stored in the memory of the control unit 37' for the skin type whose reference values correspond to the measured values of the scattering coefficient and/or absorption coefficient. As there is a clear relation between, on the one hand, the scattering coefficient and/or absorption coefficient of the skin for light of a predetermined wavelength and, on the other hand, the quantity and distribution of melanin, keratin, blood and water in the skin, there is also a clear relation between, on the one hand, said scattering coefficient and/or absorption coefficient and, on the other hand, the pulse dose from the laser source 9' that is permissible for the skin. In this manner, the pulse dose that is permissible for the skin can be reliably determined by means of the detector 55. By means of the detector 55, the values of the scattering coefficient and/or absorption coefficient are measured for two different wavelengths of the light, green light in the example shown, which has a comparatively short wavelength, and red light which has a comparatively long wavelength. The combination of the values of these coefficients for said two types of light is very specific to the skin type, so that the permissible pulse dose can be established in a very accurate manner. It is noted, however, that the invention also comprises embodiments with a detector that measures the scattering coefficient and/or absorption coefficient for only one value or for more than two values of the wavelength. It is further noted that the structure of the detector 55 is simple since the light sensor 61 is shared by the two light sources 57, 59. However, the invention also comprises embodiments wherein a separate light sensor is used for each light source 57, 59, which light sensor is, for example, sensitive only to light of the wavelength of the associated light source. The invention further also comprises embodiments wherein the detector is provided with a single light source and with a number of light sensors co-operating with the light source, which light sensors are arranged at mutually different distances from the light source. Such a detector is capable of more accurately measuring the scattering and/or absorption coefficient because information about the variation of said coefficients as a function of the depth below the skin surface can be derived from the differences between the amounts of light measured by the individual light sensors. The LEDs and photodiode used in the detector 55 are comparatively simple and have small dimensions, as a result of which both the cost-price and the dimensions of the detector 55 are limited.

In a third example of a device 53' in accordance with the invention, the biophysical property, on the basis of which the permissible pulse dose of the laser pulses is established, is a reflection coefficient of the skin 7' for light of a predetermined wavelength. As shown in FIG. 3, the device 53' is substantially equal to the above-described device 53 in accordance with the second example. The device 53' mainly differs from the device 53 in that the device 53' is provided with a detector 75, instead of the detector 55, which can suitably be used to measure the reflection coefficient of the skin 7' for light of a predetermined wavelength. Therefore, in the following, only the detector 75 of the device 53' will be discussed, which detector is diagrammatically shown in FIG. 5. The detector 75 comprises, in the example shown, two light sources 77, 79 for light having two different, predetermined wavelengths, which light sources are two LEDs in the example shown. The detector 75 further comprises a single light sensor 81, which is a photodiode in the example shown, that is arranged between the two light sources 77, 79. The light sources 77, 79 and the light sensor 81 are each arranged in a separate chamber 83, 85, 87 of the detector 75, as a result of which the light sensor 81 is optically separated from the light sources 77, 79. As shown in FIG. 5, light beams 89, 91 from the light sources 77, 79 are capable of reaching the light sensor 81 through reflection via the surface of the skin 7'. The detector 75 further comprises an electrical circuit 93 which successively activates the two light sources 77, 79 for a short period of time by means of two electrical signals $u'_{LED1}$ and $u'_{LED2}$. As a result, the circuit 93 successively receives two electrical signals $u'_{PD1}$ and $u'_{PD2}$ from the light sensor 81, which correspond to the amounts of light received by the light sensor 81 from the two light sources 77 and 79, respectively, through reflection via the skin 7'. The circuit 93 subsequently establishes the values of the reflection coefficient of the skin 7' for said two different wavelengths of the light sources 77 and 79 by comparing the amounts of light received with the amounts of light generated by the light sources 77, 79, which amounts of light are determined by the signals $u'_{LED1}$ and $u'_{LED2}$. The values of the reflection coefficient thus measured are converted by the circuit 93 into an electrical signal $u'_{CO}$ which, as shown in FIG. 3, is received by the control unit 37' of the device 53'. The control unit 37' comprises a comparator, not shown in the Figures, which compares the measured values of the reflection coefficient with reference values, which have been previously empirically established for a large number of skin types and stored in a memory of the control unit 37'. The control unit 37' determines that the permissible pulse dose from the laser source 9' is the pulse dose that is stored in the memory of the control unit 37' for the skin type whose reference values correspond to the measured values of the reflection coefficient. As there is a clear relation between, on the one hand, the reflection coefficient of the skin for light of a predetermined wavelength and, on the other hand, the quantity and distribution of melanin, keratin, blood and water in the skin, there is also a clear relation between, on the one hand, said reflection coefficient and, on the other hand, the pulse dose from the laser source 9' that is permissible for the skin. In this manner, the pulse dose that is permissible for the skin 7' can be reliably determined by means of the detector 75. In the example shown, this reliability is further improved in that the detector 75 measures the reflection coefficient for two different values of the wavelength, i.e., in the example, yellow light, which has a comparatively short wavelength, and red light which has a comparatively long wavelength. It is noted that the invention also comprises modifications of the detector 75, such as modifications as described hereinabove with respect to the detector 55.

In the above-discussed examples of a device 1, 53, 53' in accordance with the invention, the device 1, 53, 53' always comprises a detector 43, 55, 75 for measuring a biophysical property of the skin 7, 7', the control unit 37, 37' establishing a pulse dose from the laser source 9, 9' that is permissible for the skin 7, 7' on the basis of the value of the property measured by means of the detector 43, 55, 75. In the device 1, the measured biophysical property is the temperature of the skin 7, 7' resulting from exposure to at least one test radiation pulse of a predetermined pulse dose, in the device 53, the biophysical property is the scattering and/or absorption coefficient of the skin 7, 7' for light of a predetermined wavelength, and in the device 53', the biophysical property is the reflection coefficient of the skin 7, 7' for light of a predetermined wavelength. It is noted that the invention also comprises embodiments wherein a different type of biophysical property is measured by means of a suitable detector, on the basis of which biophysical property the control unit determines the permissible pulse dose. An alternative biophysical property is, for example, the electrical resistance of the skin, but the invention is not limited to this example nor to the above-mentioned examples. It is noted that, in general, the best results are achieved if a biophysical property is measured, as the basis for establishing the permissible pulse dose, which biophysical property is related to the quantity and distribution of the above-mentioned substances in the skin, in particular melanin, the relation of which to the permissible pulse dose can be accurately empirically established beforehand.

The above-discussed devices 1, 53 and 53' in accordance with the invention are laser epilation devices. However, the invention also comprises other types of hair removing devices wherein hairs are shortened or removed by means of radiation pulses. An example of such hair removing devices is a laser shaver. The operation of such a laser shaver substantially corresponds to the operation of the above-discussed laser epilation devices, however, the target position of the laser beam of the laser shaver is not in the hair root but in a position on the hair just above the surface of the skin. Another type of hair removing device, to which for example the invention applies, is a flashlight epilation device. The fourth example of a device 95 in accordance with the invention, as shown in FIG. 6, is an example of such a flashlight epilation device. The device 95 comprises a housing 97 wherein a frame 99 is arranged. A chamber 101 is provided in the frame 99, in which chamber a flashlight 103 is arranged as the radiation source, which radiation source is a Xenon lamp in the example shown. The chamber 101 is filled with a cooling liquid for the flashlight, the cooling liquid being water in the example shown. The chamber 101 has a parabolically-shaped wall 105, which is covered with a reflective material and thus serves as a reflector or directing element for the light generated by the flashlight. The chamber 101 is shut off by a transparent plate 107, which plate is a long-wave band-pass filter in the example shown. The device 95 further comprises an optical waveguide 109 which opens into an exit opening 111. Around the exit opening 111 there is provided a skin contact element 113 wherein, near the exit opening 111, a detector 115 is provided of a type similar to the above-described detector 43, 55 or 75. In operation, the flashlight 103 generates a series of light pulses having a predetermined pulse dose, i.e. a predetermined pulse duration and intensity. The light pulses are directed to the exit opening 111 by the wall 105 and reach the exit opening 111 via the transparent plate 107 and the optical waveguide 109. The frequency of the light pulses is such that the light pulses are absorbed, in particular, by the hair roots present in the skin, so that the hair roots are heated and die. For a more detailed explanation of the operation of the device 95, which is only briefly described herein, reference is made to EP-A-0 885 629. The pulse dose is such that a predetermined pulse dose that is the maximum permissible pulse dose for the skin is not exceeded. The maximum permissible pulse dose is established, in a manner comparable to that used in the above-described examples 1, 53, 53', by a control unit, not shown, of the device 95 on the basis of a measurement of a biophysical property of the skin, which measurement is carried out by means of the detector 115.

The devices 1, 53, 53' and 95 discussed hereinabove all are hair removing devices. It is finally noted that the invention also comprises other types of devices for treating skin by means of radiation pulses. Examples of such devices are devices for the medical treatment of skin by means of radiation pulses, such as by means of laser pulses, light flashes, or other types of radiation pulses having a comparatively high intensity. Such devices are used, for example, for treating birthmarks, such as naevus pigmentosus and naevus vinosus, present on the skin, psoriasis, or aberrations of blood vessels present in the skin. Other examples of such devices include devices for skin-rejuvenation cures by means of radiation pulses.

What is claimed is:

1. A device for treating skin by radiation comprising:
   a housing, the housing accommodating a radiation source;
   means for detecting a value or condition of a biophysical property of the skin,
   means for generating an input signal corresponding to a value or condition of the biophysical property,
   means for processing the input signal to determine a radiation dose that is permissible for application of radiation throughout treatment of the skin,
   means for generating an output signal corresponding to the permissible radiation dose,
   means for controlling the radiation source based on the output signal to enable a pulse dose no greater than the radiation dose from the radiation source that is permissible for the skin.

2. The device of claim 1, wherein the radiation source is not enabled to activate one or more pulse doses delivering to the skin a radiation dose greater than the radiation dose that is permissible for application of radiation throughout a treatment of the skin.

* * * * *